(12) United States Patent
Kim et al.

(10) Patent No.: US 7,981,208 B2
(45) Date of Patent: *Jul. 19, 2011

(54) GAMMA RAY-SENSITIVE PHTHALOCYANINE COMPOUND OF POLY CROSS-LINKING TYPE AND INK COMPOSITION COMPRISING THE SAME

(75) Inventors: Shi Surk Kim, Asan-si (KR); Kyung Mi Lee, Incheon (KR); Ku Won Seo, Daejeon (KR); Sang Geun Lee, Daejeon (KR); Won Gyun Choe, Daejeon (KR); Sun Hong Yoon, Seoul (KR); Soo Dong Kim, Uijeongbu-si (KR)

(73) Assignees: Nanocms Co., Ltd. (KR); Korea Minting and Security Printing Corp. (KR)

(*) Notice: Subject to any disclaimer, the term of this patent is extended or adjusted under 35 U.S.C. 154(b) by 407 days.

This patent is subject to a terminal disclaimer.

(21) Appl. No.: 12/112,418

(22) Filed: Apr. 30, 2008

(65) Prior Publication Data

US 2009/0326207 A1     Dec. 31, 2009

(30) Foreign Application Priority Data

Apr. 30, 2007   (KR) .................. 10-2007-0042163

(51) Int. Cl.
*C09D 11/02*   (2006.01)
*C09B 47/04*   (2006.01)

(52) U.S. Cl. .................. 106/31.49; 106/31.78; 540/139; 540/140

(58) Field of Classification Search .............. 106/31.49, 106/31.78; 540/122, 139, 140
See application file for complete search history.

(56) References Cited

U.S. PATENT DOCUMENTS 4,223,123 A * 9/1980 Keller et al. .................. 528/210
(Continued)

FOREIGN PATENT DOCUMENTS

| KR | 10-2003-0058988 A | 7/2003 |
|---|---|---|
| WO | 02/053570 A1 | 7/2002 |
| WO | 2004/039913 A2 | 5/2004 |

(Continued)

*Primary Examiner* — Helene Klemanski
(74) *Attorney, Agent, or Firm* — Park & Associates IP Law, P.C.

(57) ABSTRACT

The present invention relates to phthalocyanine compound of poly cross-linking type which is represented with the below formula 1 and is useful for preventing forgery and alternation due to a rapid velocity being responded to a gamma ray of Neutron, and an ink composition comprising it.

[formula 1]

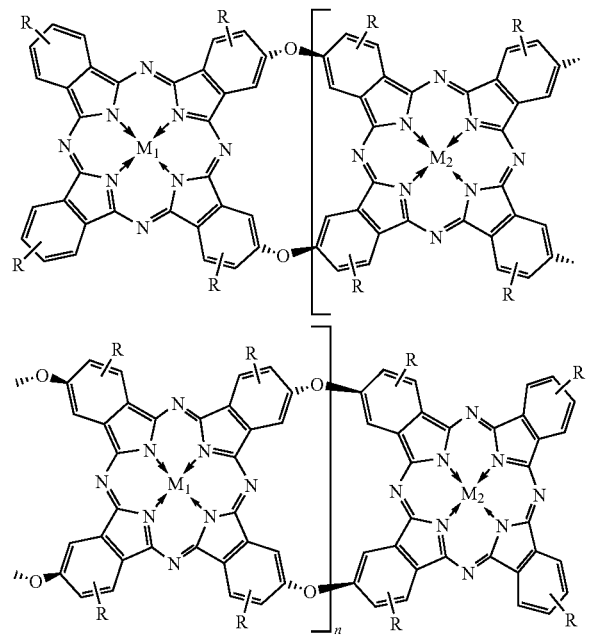

wherein, $M_1$ and $M_2$ are any one selected from a group consisted of a metal, a metal oxide or a metal halide respectively and may be same or different, R is a hydrogen atom, a halogen atom, a hydroxyl group, an amino group, a hydroxysulfonyl group, an aminosulfonyl group, or an alky group having a substituent group having from 1 to 20 carbon atoms, and n is an integer of 0~3.

9 Claims, 10 Drawing Sheets

U.S. PATENT DOCUMENTS

| | | | |
|---|---|---|---|
| 4,311,775 A * | 1/1982 | Regan | 430/37 |
| 4,943,681 A * | 7/1990 | Sato et al. | 540/140 |
| 5,110,916 A | 5/1992 | Yamamoto et al. | |
| 5,456,998 A * | 10/1995 | Burt et al. | 430/58.8 |
| 5,675,001 A * | 10/1997 | Hoffman et al. | 540/139 |
| 6,174,400 B1 | 1/2001 | Krutak, Sr. et al. | |
| 7,163,772 B2 * | 1/2007 | Yamasaki et al. | 540/139 |
| 7,524,367 B2 * | 4/2009 | Ihm et al. | 106/31.49 |
| 7,550,038 B2 * | 6/2009 | Kim et al. | 106/31.49 |
| 2004/0146793 A1 * | 7/2004 | Yamasaki et al. | 430/59.4 |
| 2008/0184909 A1 * | 8/2008 | Kim et al. | 106/31.13 |
| 2009/0076192 A1 * | 3/2009 | Ihm et al. | 523/135 |

FOREIGN PATENT DOCUMENTS

| | | |
|---|---|---|
| WO | 2004/106436 A1 | 12/2004 |
| WO | 2005/081240 A2 | 9/2005 |
| WO | 2007/009101 A2 | 1/2007 |
| WO | WO 2007/013732 * | 2/2007 |

* cited by examiner

GAMMA RAY-SENSITIVE PHTHALOCYANINE COMPOUND OF POLY CROSS-LINKING TYPE AND INK COMPOSITION COMPRISING THE SAME

THE NAMES OF THE PARTIES TO A JOINT RESEARCH AGREEMENT

The claimed invention has been made by or on behalf of the parties to a joint research agreement, namely, NANOCMS CO., LTD. (formerly CMS TECHNOLOGY INC.) and KOREA MINTING AND SECURITY PRINTING CORP., which was executed on Jul. 4, 2006.

FIELD OF THE INVENTION

The present invention relates to phthalocyanine compound of poly cross-linking type which is useful for preventing forgery and alternation due to a rapid velocity being responded to a gamma ray of Neutron, and an ink composition comprising it.

BACKGROUND OF THE INVENTION

As being well known, it is open to possibility of forgery and alternation for all sorts of cards such as a cash card or credit card, all sorts of certificate such as a passport, an insurance policy and a driving license, checks or securities, paper money, an industrial product material being rendered an information such as a brand or produced record, a food label being rendered an information such as producing district or producing time.

To prevent forgery or alternation for such matters, it has been conventionally carried to attach a mark having magnetic properties or a mark absorbing and reflecting an electromagnetic wave or a mark emitting fluorescence by a visual ray, and then distinguish an authentic matter from a spurious article which the said mark is not attached or the other mark is attached. For example, it may be consisted of irradiating an electromagnetic wave of a determined wave area, detecting a fluorescence being radiated from the said information rendering materials by such irradiation of an electromagnetic wave, and discriminating forgery or alternation for such matters according to the said detected result of fluorescence.

In these days, an automatic sorting or identifying elements have been used by enabling to measure absorption and reflection of infrared ray being ranged of wavelength (700~1600 nm) with a device since a semiconductor laser having a range of infrared ray of the said wavelength that can not be recognized with a naked eye had been developed as a light source to recognize and detect an image.

To carry out such discrimination of alternation promptly, it is necessary to use the materials that enable to detect in real time as respond within short time with employment of the material being responsive to a gamma ray. However, there had been not known the materials that respond to high energy among the known compounds being used in a mark for preventing forgery or alternation so that radioactive elements or compounds that respond with absorption of low energy have been used in the form of combination, which makes it difficult to prompt decision of forgery or alternation because the velocity responsive to a gamma ray is slow as well as an amounts of absorption are of small quantity.

SUMMARY OF THE INVENTION

Accordingly, the present invention has been made in view of the above-mentioned problems occurring in the prior art, and it is an object of the present invention to provide phthalocyanine compound of poly cross-linking type which enables to discriminate forgery and alternation promptly due to a rapid velocity being responded to a gamma ray of Neutron and respond to high energy.

Also, it is the other object of the present invention to provide an ink composition comprising the said gamma ray-sensitive phthalocyanine compound of poly cross-linking type.

To accomplish the above object, according to the present invention, there is provided gamma ray-sensitive phthalocyanine compound of poly cross-linking type characterized in that it is represented with the below formula 1.

[formula 1]

wherein, $M_1$ and $M_2$ are any one selected from a group consisted of a metal, a metal oxide or a metal halide respectively and may be same or different, R is a hydrogen atom, a halogen atom, a hydroxyl group, an amino group, a hydroxysulfonyl group, an aminosulfonyl group, or an alky group having a substituent group having from 1 to 20 carbon atoms, and n is an integer of 0~3.

Also, to accomplish the other object, according to the present invention, there is provided an ink composition characterized in that it comprises the said gamma ray-sensitive phthalocyanine compound of poly cross-linking type.

The present invention will be now illustrated by the below description in detail.

The gamma ray-sensitive phthalocyanine compound of poly cross-linking type according to the present invention has a configuration of the said formula 1. The phthalocyanine compound of poly cross-linking type having such configuration is responsive to a gamma ray. Especially, it exerts a property that is responsive to a gamma ray of Neutron which the compounds being known up to now do not respond. Therefore, the compounds of formula 1 may be effectively used for preventing forgery and alternation because it respond to a gamma ray rapidly so that enables prompt discrimination for forgery and alternation of articles. Such property sensitive for a gamma ray can be verified with radiation of a gamma ray of Neutron.

In the said formula 1, the metals that may be applied to $M_1$ and $M_2$ can be selected from Lithium, beryllium, sodium, magnesium, aluminum, potassium, calcium, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, barium, lanthanum, cesium, praseodymium, samarium, europium, gadolinium, terbium, dysprosium, holmium, erbium, thulium, ytterbium, ruthenium, hafnium, tantalum, tungsten, rhenium, osmium, iridium, platinum, gold, mercury, thallium, lead, bismuth, actinium, thorium, protactinium, uranium, neptunium and americium.

In the said formula 1, $M_1$ and $M_2$ may preferably be metals or metallic oxides selected from samarium, europium, rubidium, cesium, gadolinium or dysprosium.

More preferably, it is phthalocyanine compound of poly cross-linking type represented with the below formula 2 which, in the said formula 1, $M_1$ and $M_2$ are each dysprosium and R is a hydrogen atom, or it is phthalocyanine compound of poly cross-linking type represented with the below formula 3 which, in the said formula 1, $M_1$ and $M_2$ are each gadolinium and R is a hydrogen atom.

[formula 3]

wherein, n is an integer of 0~3.

More preferably, it is phthalocyanine compound of poly cross-linking type represented with the below formula 4 which, in the said formula 1, $M_1$ is cesium and $M_2$ is rubidium and R is a hydrogen atom.

[formula 2]

wherein, n is an integer of 0~3.

[formula 4]

wherein, n is an integer of 0~3.

The said phthalocyanine compound of poly cross-linking type of formula 1 according to the present invention can be easily prepared by the well known process of preparing phthalocyanine compound of poly cross-linking type. More concretely, phthalic anhydride of the below formula 5, urea, metallic slats or metallic chlorides corresponding to M1 and M2, a solvent having high boiling point and a reactive initiator are mixed at the normal temperature, heated and refluxed to 230~250° C. and then reacted during 6~8 hours. After reaction, the mixture is filtered while being maintained to a temperature of 70~100° C., and washed with dilute acid solution and alkaline solution respectively at 65~70° C. to obtain a cake which an un-reacted materials are removed. The obtained cake is dispersed in 5 weight % of aqueous ethylene glycol to 5~10 w/w %, treated with heat during 2 hours while maintaining to 80~120° C., and filtered, and then dispersed again in acetone and dimethyl acetamide respectively. The dispersed solution is purified by using a Soxhlet device at 45~175° C., and then dried to obtain the desired products easily.

[formula 5]

wherein, R is a hydrogen atom, a halogen atom, a hydroxyl group, an amino group, a hydroxysulfonyl group, an aminosulfonyl group, or an alky group having a substituent group having from 1 to 20 carbon atoms.

At the above procedure, a cautious attention in storage of phthalic anhydride represented with formula 5 should be provided not to be dried and introduced water moisture since its reactivity is reduced when water moisture is introduced. Urea may use a conventional product. And, as a reactive solvent, any one selected from α-methylnaphthalene, α-chloronaphthalene, dichlorobenzene, DMF, n-alkylbenzene or ethylene glycol which is a solvent having low polarity and high boiling point, may be used.

Phthalocyanine compound of poly cross-linking type prepared with the said procedure represent a property that absorbs a wavelength of near infrared ray area of 750~950 nm with high absorbing capacity as well as a rapid responsive velocity for a gamma ray of Neutron. Therefore, phthalocyanine compound of poly cross-linking type according to the present invention may be effectively used as sensitive materials of a gamma ray in articles for preventing forgery. Especially, it may be effectively used in an ink or a paint composition.

Therefore, according to the present invention, an ink composition comprising the said gamma ray-sensitive phthalocyanine compound of poly cross-linking type which has a configuration of the said formula 1 and respond to a gamma ray is provided.

Phthalocyanine compound of poly cross-linking type according to the present invention may exert a sufficient effect only by being added with 0.01~5 weight part against 100 weight part of an ink composition, and may be effectively used in documents for fraud protection, copy protection and prevention of forgery and alternation since it exhibits a rapid responsive velocity for a gamma ray of Neutron. At this time, the said ink composition may be used to any one among inks of various kinds comprising an ink for a conventional dyes type inkjet, an ink for a conventional pigment type inkjet, an ink for a screen print and the like.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE INVENTION

The following Examples will afford a better understanding of the present invention. These Examples, which do not limit the scope of the invention, are only intended to illustrate the present invention in detail.

Example 1

Preparation of Poly Cross-Linking Dysprosium Phthalocyanine 148 weight part of phthalic anhydride, 425 weight part of urea, 150 weight part of dysprosium 6 hydrate, 30 weight part of anhydrous dysprosium salt, 1.8 weight part of ammonium molybdenite, and 1500 weight part of alkyl benzene are mixed sufficiently, and then raised temperature up to 200° C. during 4 hours and reacted during 3 hours. During reaction, a nitrogen gas is introduced with velocity of 300 ml/min. And then it is filtered with 500 weight parts of 10% hydrochloric acid solution and 10% sodium hydroxide alkaline solution respectively and washed water several times. After being dried in a dehydrator at 80° C. to be constant weight completely, the obtained dried matters dispersed in aqueous solution of 10 weight % ethylene glycol to 10 w/w % and then treated during 1 hour at 80° C. After heat treatment, it is filtered, and washed with 500 ml of water at 100° C. two times and then dried during 24 hours at 80° C. The resultant matters are charged into 300 weight parts of acetone and the mixture is purified by using a Soxhlet device, and then dried. The resultant matters are again charged into 300 weight part of dimethylformamide and the mixture is purified by using a Soxhlet device, and then dried to obtain the desired products.

Figure 1A:
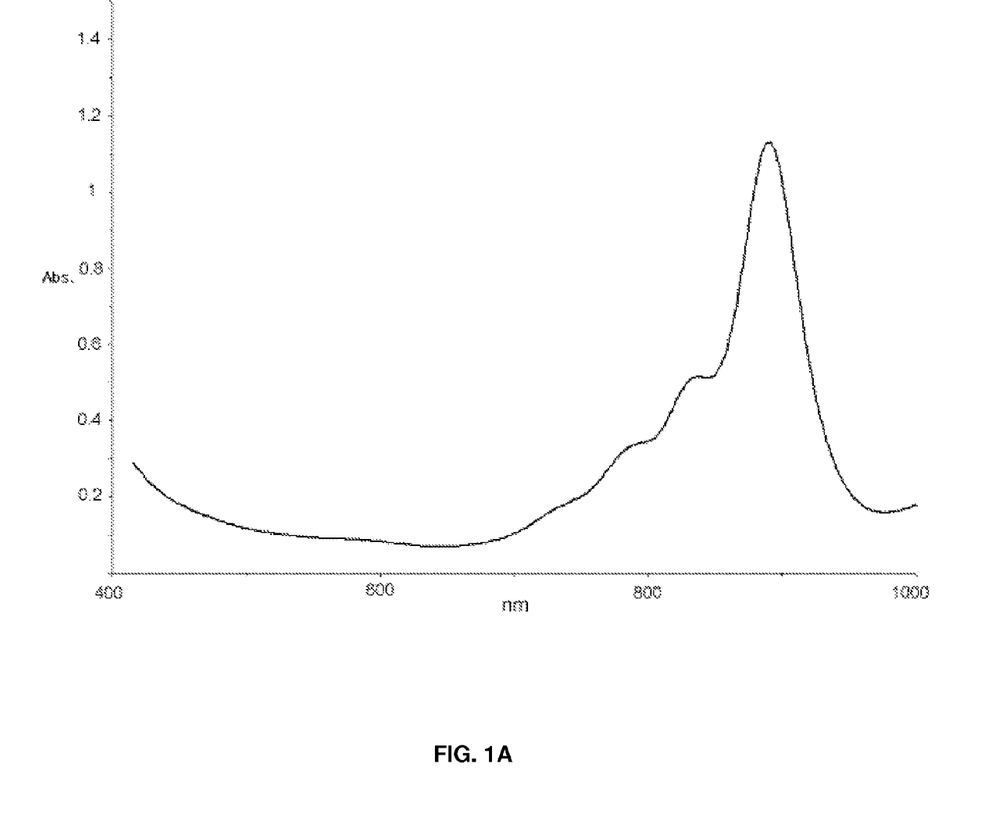
FIG. 1a and 1b are a graph showing infrared ray absorbing wavelength and reflectivity of poly cross-linking dysprosium phthalocyanine compound prepared at Example 1.
Figure 1B:
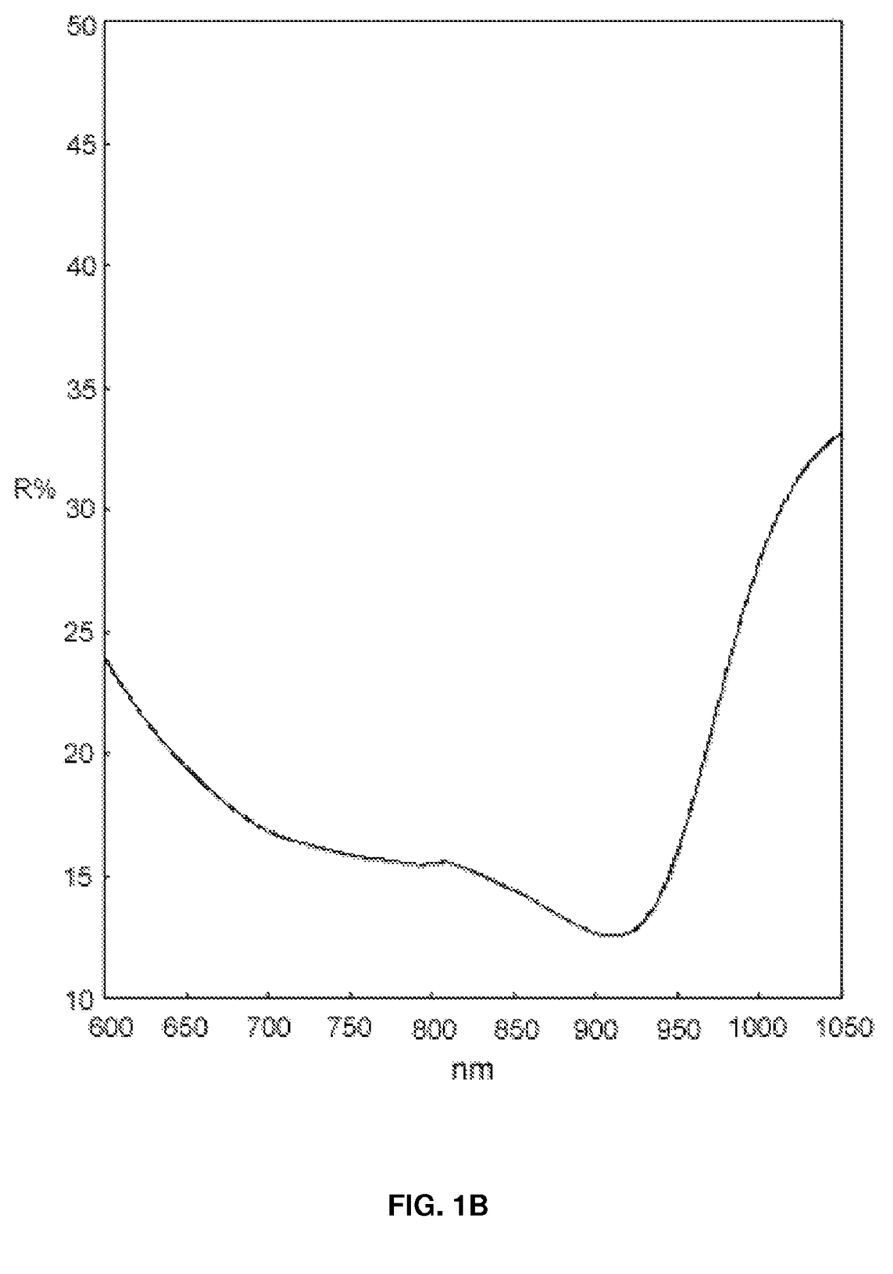
Figure 2A:
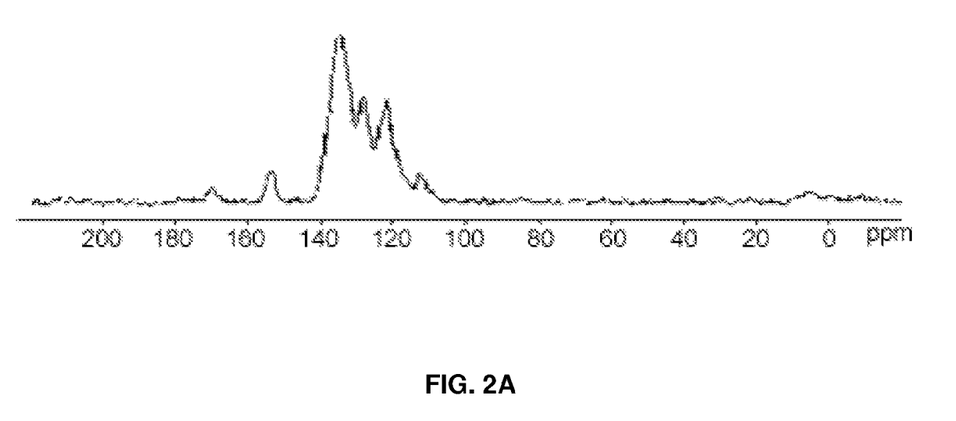
FIGS. 2a and 2b are a graph showing $^{13}$NMR and FT-IR spectrum of poly cross-linking dysprosium phthalocyanine compound prepared at Example 1.
Figure 2B:
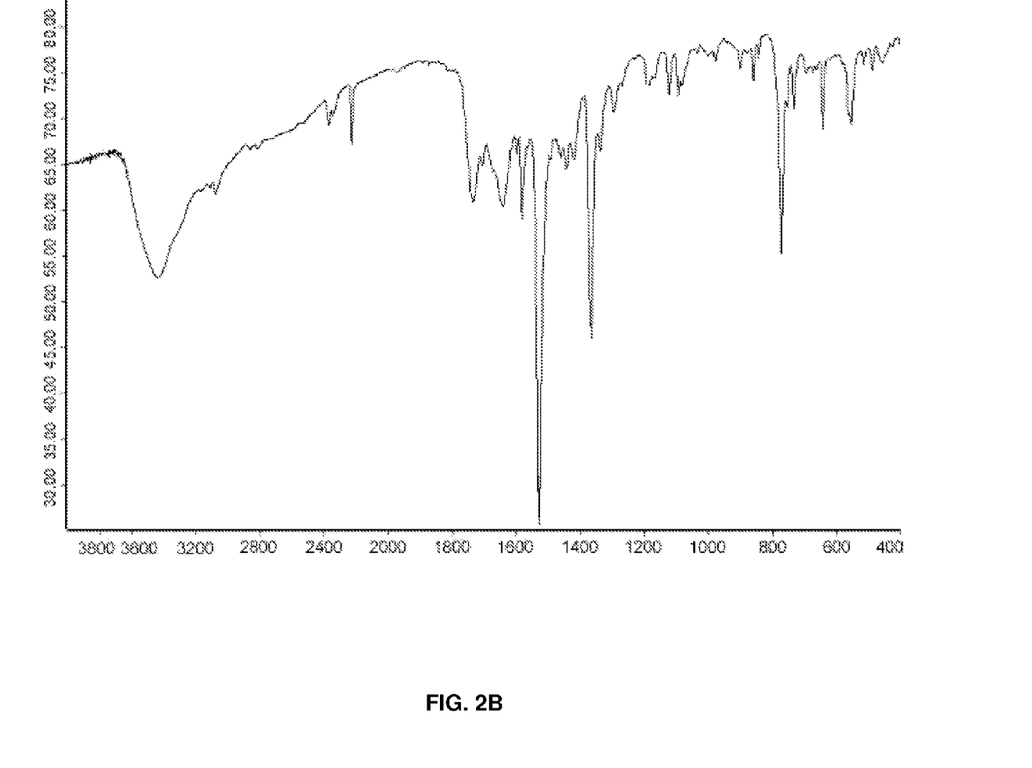

Infrared ray absorbing wavelength and reflectivity of the compound obtained by such procedure are shown in FIG. 1a and 1b, and together with these, $^{13}$NMR and FT-IR spectrum are also shown in FIGS. 2a and 2b. Also, absorbance data measured with UV-visible spectrophotometer is shown in table 1, and together with these, a result of atom analysis is also shown in table 2.

The result can confirm the obtained compound as phthalocyanine compound of poly cross-linking type having configuration of the below formula 6.

Example 2

Preparation of Poly Cross-Linking Gadolinium Phthalocyanine

148 weight part of phthalic anhydride, 425 weight part of urea, 148 weight part of gadolinium 6 hydrate, 20 weight part of anhydrous gadolinium salt, 1.8 weight part of ammonium molybdenite, and 1500 weight part of alkyl benzene are mixed sufficiently, and then raised temperature up to 200° C. during 4 hours and reacted during 3 hours. During reaction, a nitrogen gas is introduced with velocity of 300 ml/min. And then it is filtered with 500 weight parts of 10% hydrochloric acid solution and 10% sodium hydroxide alkaline solution respectively and washed water several times. After being dried in a dehydrator at 80° C. to be constant weight completely, the obtained dried matters dispersed in aqueous solution of 10 weight % ethylene glycol to 10 w/w % and then treated during 1 hour at 80° C. After heat treatment, it is filtered, and washed with 500 ml of water at 100° C. two times and then dried during 24 hours at 80° C. The resultant matters are charged into 300 weight parts of acetone and the mixture is purified by using a Soxhlet device, and then dried. The resultant matters are again charged into 300 weight part of dimethylformamide and the mixture is purified by using a Soxhlet device, and then dried to obtain the desired products.

Figure 3A:
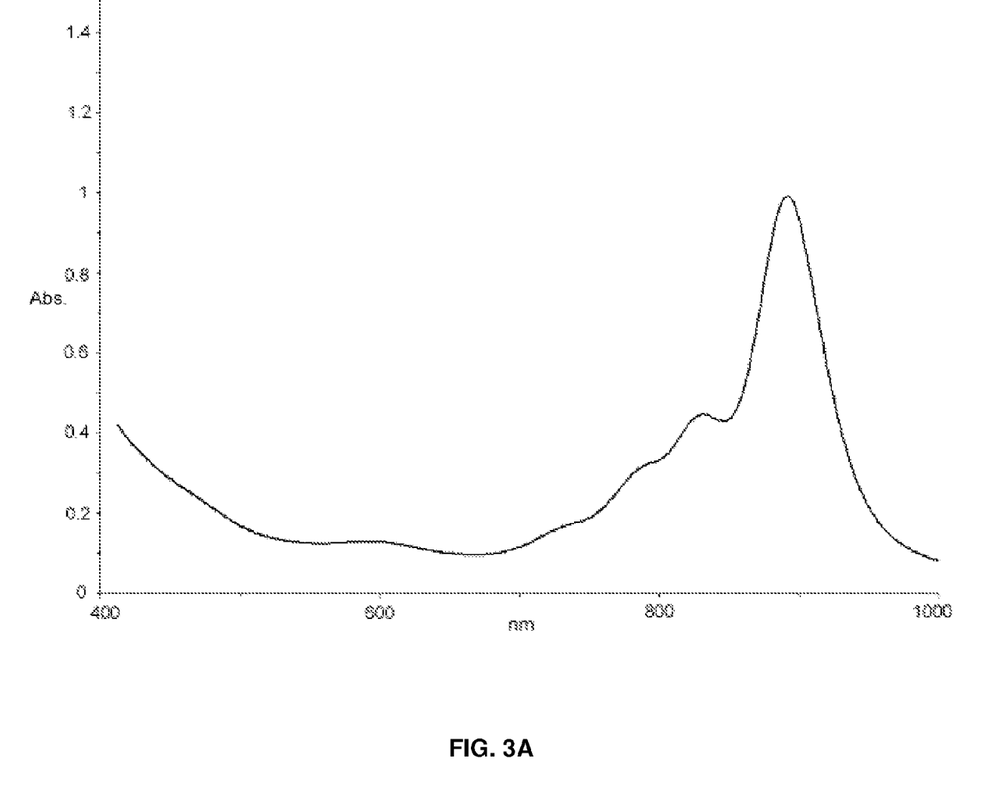
FIGS. 3a and 3b are a graph showing infrared ray absorbing wavelength and reflectivity of poly cross-linking gadolinium phthalocyanine compound prepared at Example 2.
Figure 3B:
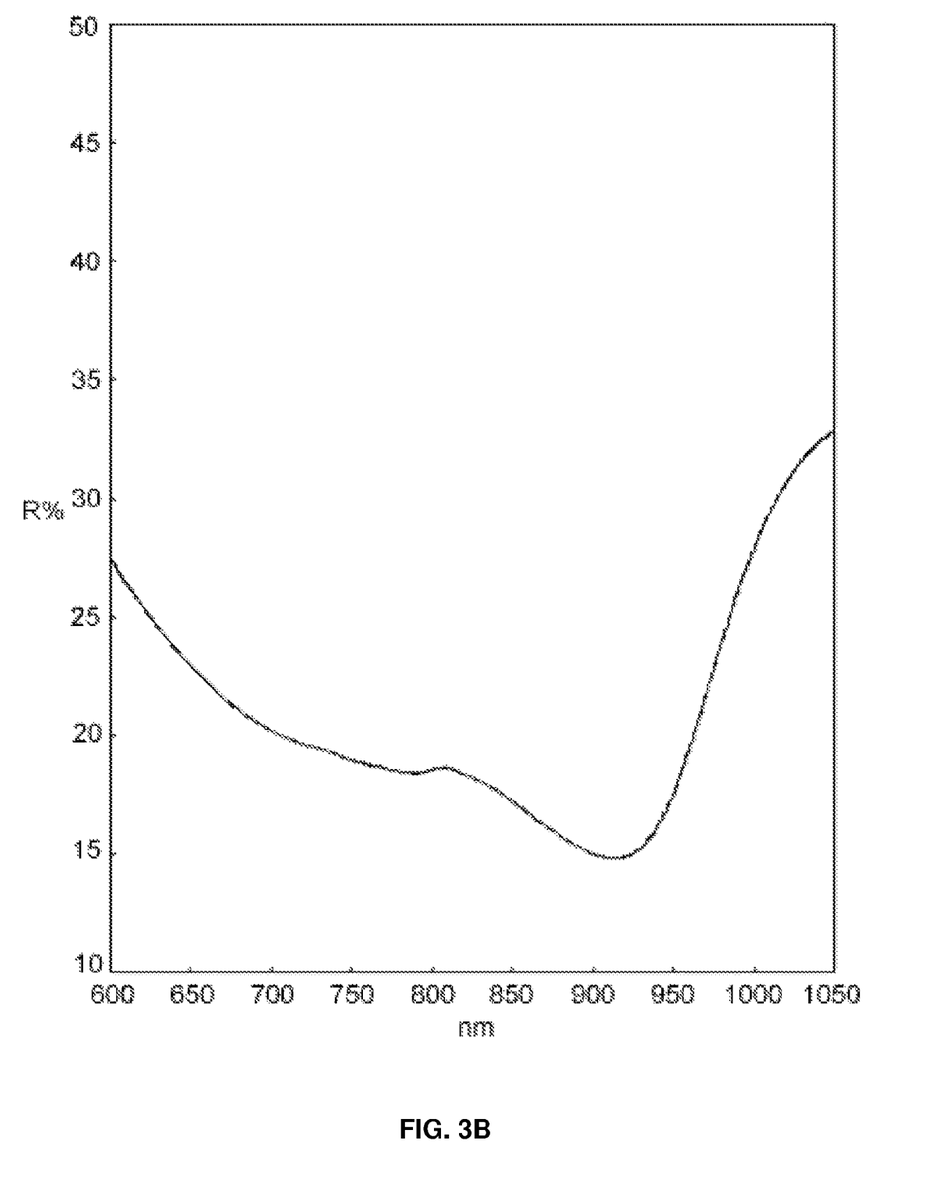

Infrared ray absorbing wavelength and reflectivity of the compound obtained by the said drying procedure are shown in FIGS. 3a and 3b. Also, absorbance data measured with UV-visible spectrophotometer is shown in table 1, and together with these, a result of atom analysis is also shown in table 2.

The result can confirm the obtained compound as phthalocyanine compound of poly cross-linking type having configuration of the below formula 7.

[formula 6]

[formula 7]

Comparative Example 1

Figure 4A:
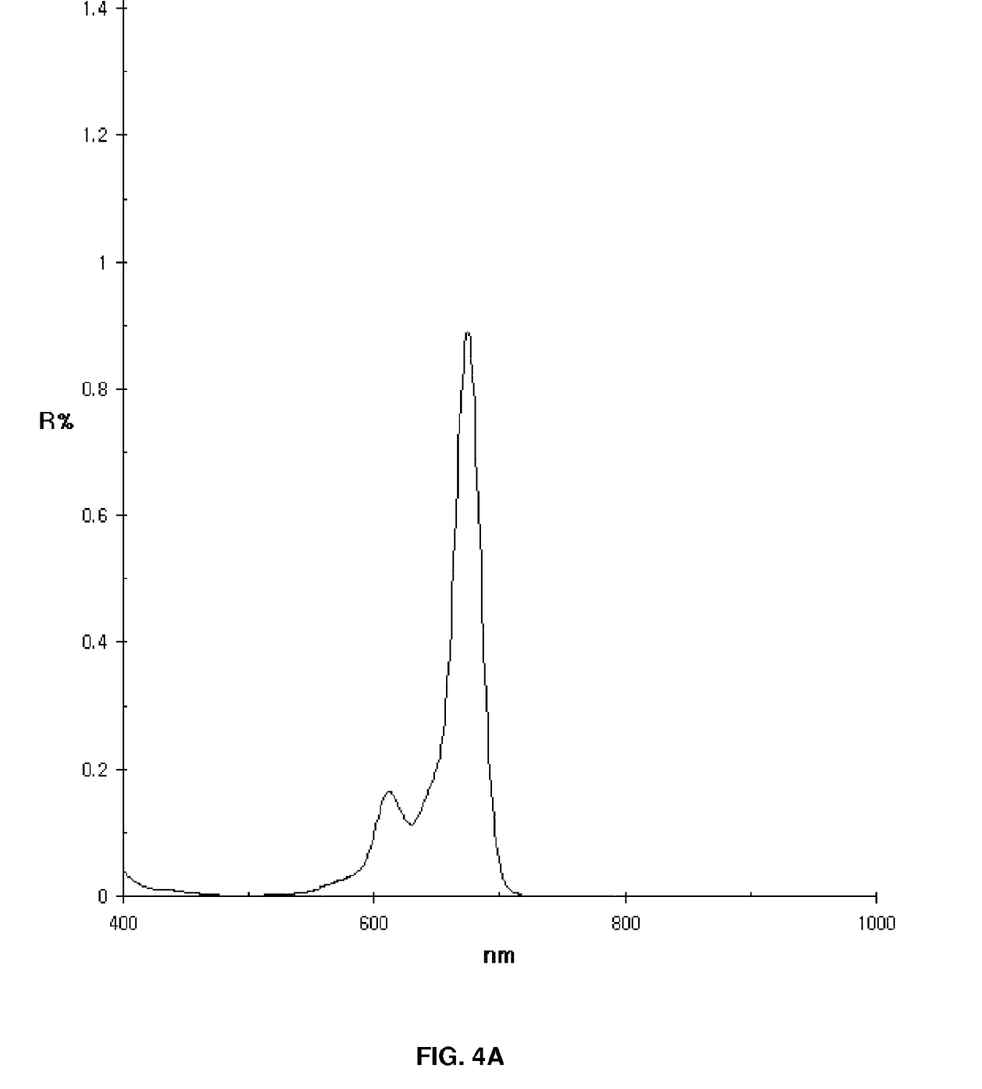
FIGS. 4a and 4b are a graph showing infrared ray absorbing wavelength and reflectivity of magnesium phthalocyanine compound prepared at Comparative example 1.
Figure 4B:
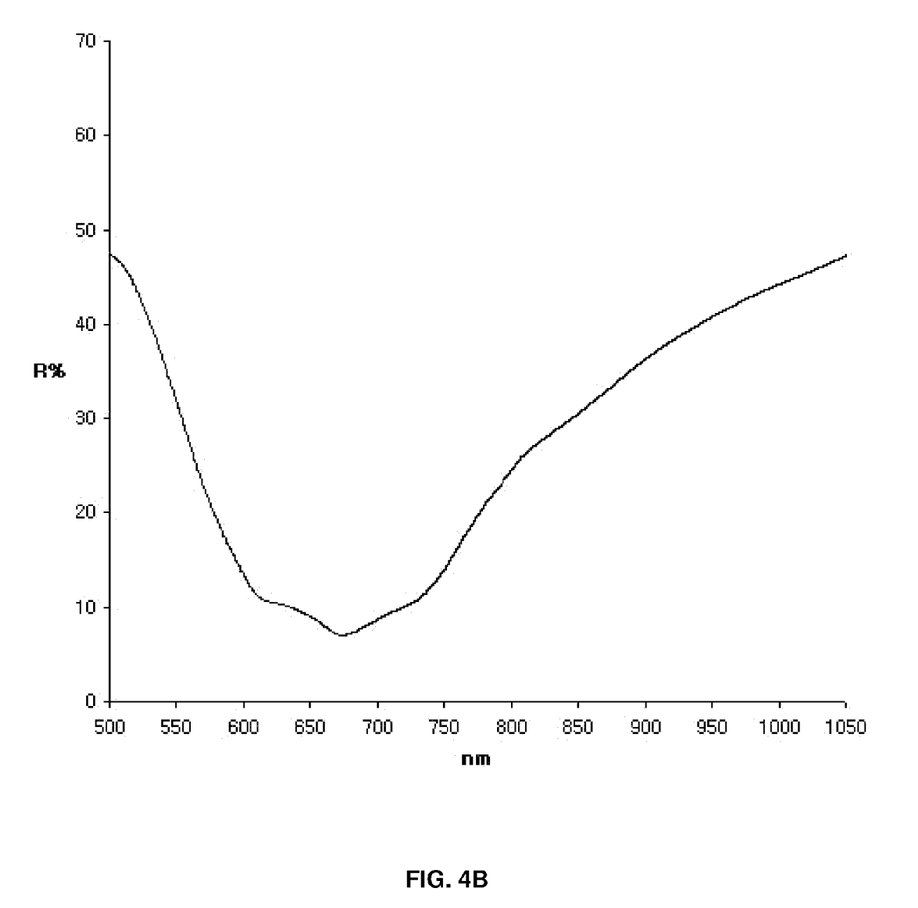
Figure 5A:
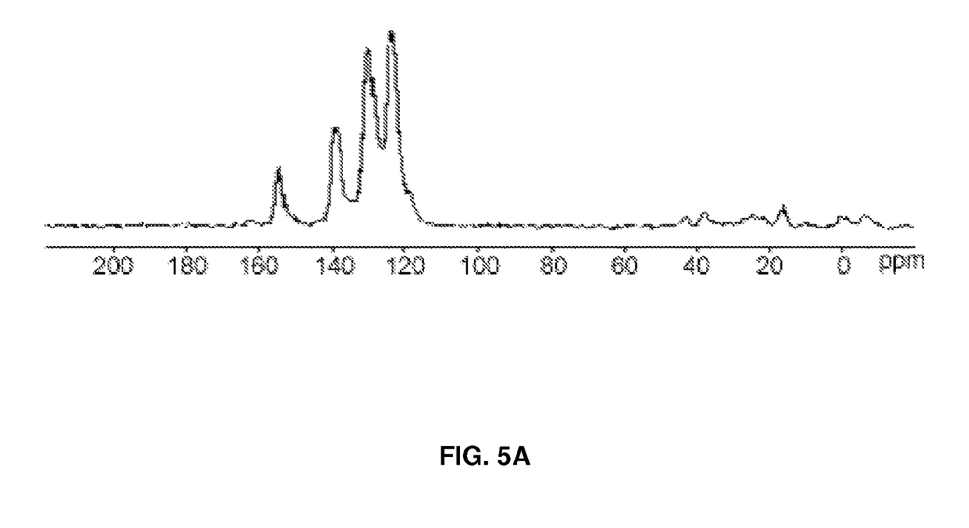
FIGS. 5a and 5b are a graph showing $^{13}$NMR and FT-IR spectrum of magnesium phthalocyanine compound prepared at Comparative example 1.
Figure 5B:
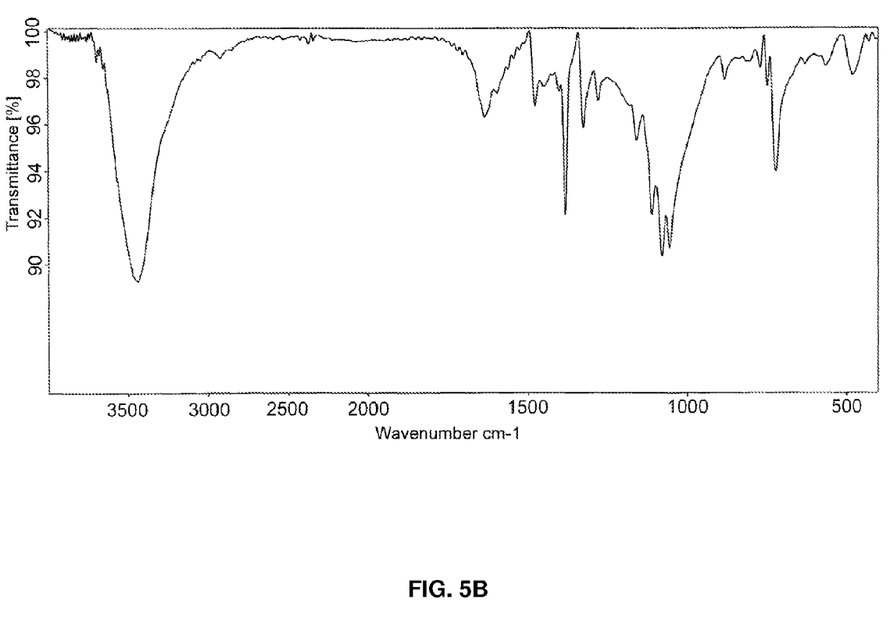

Infrared ray absorbing wavelength and reflectivity of magnesium phthalocyanine compound having configuration of the below formula 8 are shown in FIGS. 4a and 4b, and together with these, $^{13}$NMR and FT-IR spectrum are also shown in FIGS. 5a and 5b. Also, absorbance data measured with UV-visible spectrophotometer is shown in table 1.

TABLE 1

[formula 8]

| Item | Central metal ($M_1$, $M_2$) | Maximum absorbance |
|---|---|---|
| Example 1 | Dy, Dy | 894 |
| Example 2 | Gd, Gd | 884 |
| Comparative example 1 | Mg | 676 |

TABLE 2

| Item | Molecular weight | N | C | H | O | Metal |
|---|---|---|---|---|---|---|
| Example 1 | 4190.0 | 55.09 | 1.9 | 16.02 | 3.8 | 23.19 |
| Example 2 | 4158.3 | 55.5 | 1.88 | 16.14 | 3.88 | 22.6 |

FIGS. 1 to 3 as well as the above tables 1 and 2 are data that may be of help to confirm a configuration of phthalocyanine compound of poly cross-linking type prepared by examples 1 and 2 according to the present invention. Especially, as being confirmed at the above table 1, we can see that phthalocyanine compound of poly cross-linking type according to the present invention absorbs a near infrared wavelength with more higher absorbing capacity than magnesium phthalocyanine compound according to a comparative example 1 which is a conventional monomolecular form having a maximum absorbance of 890 nm.

Examples 3 to 8

An ink composition applied to a screen print was prepared according to the below table 3. The said ink composition was prepared by mixing distilled water, a pigment, a resin, a wetting agent, a stabilizer, an additive, a dispersing agent, a near infrared ray absorbing agent of a gamma ray sensitive type and solvent, and then dispersing the mixture by using a Three roll mill. At the said procedure, Green (CI. No. 36) is used as a pigment, and Alkyd varnish resin is used as a resin. Wax is used as a wetting agent, and a nonionic surfactant is used as a stabilizer. Talc is used as a additive, and BYK Chemie:BYK 910 is used as a dispersing agent, and the compound obtained from example 1 is used as a used as a sensitive agent for a gamma ray. As a solvent, cyclohexane is used.

A screen printing was carried out by the prepared ink for a screen print. A gamma ray is irradiated on the sample, that is the said printed matters, by using a high energy generator and a detector, and then it is confirmed with a detector for whether response by high energy is or not. The result is shown in the below table 3.

TABLE 3

| Item | Pigment (g) | Resin (g) | Wetting agent (g) | Stabilizer (g) | Additive (g) | Dispersing agent (g) | Sensitive agent for gamma ray (g) | Solvent (g) | sensitivity |
|---|---|---|---|---|---|---|---|---|---|
| Ex. 3 | 5 | 35 | 5 | 10 | 25 | 3 | 0.005 | 16.995 | − |
| Ex. 4 | 5 | 35 | 5 | 10 | 25 | 3 | 0.01 | 16.99 | + |
| Ex. 5 | 5 | 35 | 5 | 10 | 25 | 3 | 0.1 | 16.9 | + |
| Ex. 6 | 5 | 35 | 5 | 10 | 25 | 3 | 0.5 | 16.5 | ++ |
| Ex. 7 | 5 | 35 | 5 | 10 | 25 | 3 | 2 | 15 | ++ |
| Ex. 8 | 5 | 35 | 5 | 10 | 25 | 3 | 5 | 12 | +++ |
| Ex. 9 | 5 | 35 | 5 | 10 | 25 | 3 | 6 | 11 | +++ |

As being confirmed at the above table 3, we can see that, in case of an ink composition comprising phthalocyanine compound of poly cross-linking type according to the present invention, examples 4 to 8 which phthalocyanine compound of poly cross-linking type is added within preferable range exhibit an excellent sensitivity according to a result of irradiating a gamma ray, but example 9 which phthalocyanine compound of poly cross-linking type is added with excessive amount do not exhibit more excellent sensitivity than the said examples.

As being illustrated, the present invention has an useful effect in that it provides phthalocyanine compound of poly cross-linking type which is useful for preventing forgery and alternation due to a rapid velocity being responded to a gamma ray of Neutron, and an ink composition comprising it.

What is claimed is:

1. Gamma ray-sensitive poly cross-linking phthalocyanine compound represented by the below formula 1:

[formula 1]

wherein, $M_1$ and $M_2$ are each a metal or a metal oxide selected from the group consisting of samarium, europium, rubidium, cesium, gadolinium, and dysprosium;

R is a hydrogen atom, a halogen atom, a hydroxyl group, an amino group, a hydroxysulfonyl group, an aminosulfonyl group, or an alky group having a substituent group having from 1 to 20 carbon atoms; and n is an integer of 0~3.

2. Gamma ray-sensitive poly cross-linking phthalocyanine compound according to claim 1, wherein $M_1$ and $M_2$ are each dysprosium and R is a hydrogen atom in the formula 1, represented by the formula 2 below:

[formula 2]

wherein, n is an integer of 0~3.

3. Gamma ray-sensitive poly cross-linking phthalocyanine compound according to claim 1, wherein $M_1$ and $M_2$ are each gadolinium and R is a hydrogen atom in the formula 1, represented by the formula 3 below:

[formula 3]

wherein, n is an integer of 0~3.

4. Gamma ray-sensitive poly cross-linking phthalocyanine compound according to claim 1, wherein $M_1$ is cesium and $M_2$ is rubidium and R is a hydrogen atom in the formula 1, represented by the formula 4 below:

[formula 4]

wherein, n is an integer of 0~3.

5. An ink composition comprising a sensitive agent for a gamma ray, wherein said sensitive agent for a gamma ray is the poly cross-linking phthalocyanine compound according to claim 1.

6. An ink composition according to claim 5, wherein said poly cross-linking phthalocyanine compound is contained of 0.01~5 weight part against 100 weight part of a total ink composition.

7. An ink composition according to claim 6, wherein the said ink composition is a dye ink for inkjet printing.

8. An ink composition according to claim 6, wherein the said ink composition is a pigment ink for inkjet printing.

9. An ink composition according to claim 6, wherein the said ink composition is a screen printing ink.

* * * * *